(12) United States Patent
Van Westrenen

(10) Patent No.: US 9,115,037 B2
(45) Date of Patent: Aug. 25, 2015

(54) PROCESS FOR REMOVING OXYGENATE FROM AN OLEFIN STREAM

(71) Applicant: Shell Oil Company, Houston, TX (US)

(72) Inventor: Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/136,189

(22) Filed: Dec. 20, 2013

(65) Prior Publication Data

US 2014/0187805 A1    Jul. 3, 2014

(30) Foreign Application Priority Data

Dec. 28, 2012 (EP) .................................. 12199677

(51) Int. Cl.
| | |
|---|---|
| *C07D 301/03* | (2006.01) |
| *C07C 1/00* | (2006.01) |
| *C07C 2/00* | (2006.01) |
| *C07C 7/10* | (2006.01) |
| *C07C 1/20* | (2006.01) |
| *C07C 7/08* | (2006.01) |
| *C07C 11/04* | (2006.01) |
| *C07C 11/06* | (2006.01) |

(52) U.S. Cl.
CPC ... *C07C 7/10* (2013.01); *C07C 1/20* (2013.01); *C07C 7/08* (2013.01); *C07C 11/04* (2013.01); *C07C 11/06* (2013.01); *C07D 301/03* (2013.01)

(58) Field of Classification Search
CPC .......... C07D 301/03; C07C 7/08; C07C 7/10; C07C 1/20; C07C 11/04; C07C 11/06

USPC ........................... 549/523; 585/324, 329, 835
See application file for complete search history.

(56) References Cited

U.S. PATENT DOCUMENTS

| | | | |
|---|---|---|---|
| 4,567,029 | A | 1/1986 | Wilson et al. |
| 7,002,050 | B2 | 2/2006 | Santiago Fernandez et al. |
| 7,132,580 | B1 | 11/2006 | Senetar |

(Continued)

FOREIGN PATENT DOCUMENTS

| | | |
|---|---|---|
| WO | 03020678 | 3/2003 |
| WO | 2006020083 | 2/2006 |

OTHER PUBLICATIONS

Reichardt, Solvents and Solvent effects in Organic Chemistry, 2003, Verlag GmbH & Co., 3rd ed., p. 1-37.*

(Continued)

*Primary Examiner* — T. Victor Oh

(57) ABSTRACT

The present invention relates to a process for removing dimethylether from an olefin stream comprising dimethylether, comprising: (a) providing to an oxygenate recovery zone the olefin stream comprising dimethylether and a methanol-comprising solvent, treating the olefin stream comprising dimethylether with the methanol comprising solvent, and retrieving at least a dimethylether-depleted, methanol-comprising olefin stream; and (b) providing to the oxygenate recovery zone a non-aqueous C2 to C4 alcohol solvent and treating the dimethylether-depleted, methanol-comprising olefin stream with the non-aqueous C2 to C4 alcohol solvent, and retrieving from the oxygenate recovery zone at least an olefinic product that is depleted in dimethylether and methanol and a spent solvent comprising at least one C2 to C4 alcohol and methanol.

10 Claims, 1 Drawing Sheet

(56) References Cited

U.S. PATENT DOCUMENTS

| | | |
|---|---|---|
| 2003/0045644 A1 | 3/2003 | Mougin |
| 2007/0155999 A1 | 7/2007 | Pujado et al. |
| 2007/0203380 A1 | 8/2007 | Vora et al. |
| 2009/0223870 A1 | 9/2009 | Birke et al. |

OTHER PUBLICATIONS

Nowowiejski et al., An overview of oxygenates in olefins units in relation to corrosion, fouling, product specifications, and safety, Presentation at American Institute of Chemical Engineers 2003 Spring National Meeting, New Orleans, USA, in particular p. 16.

* cited by examiner

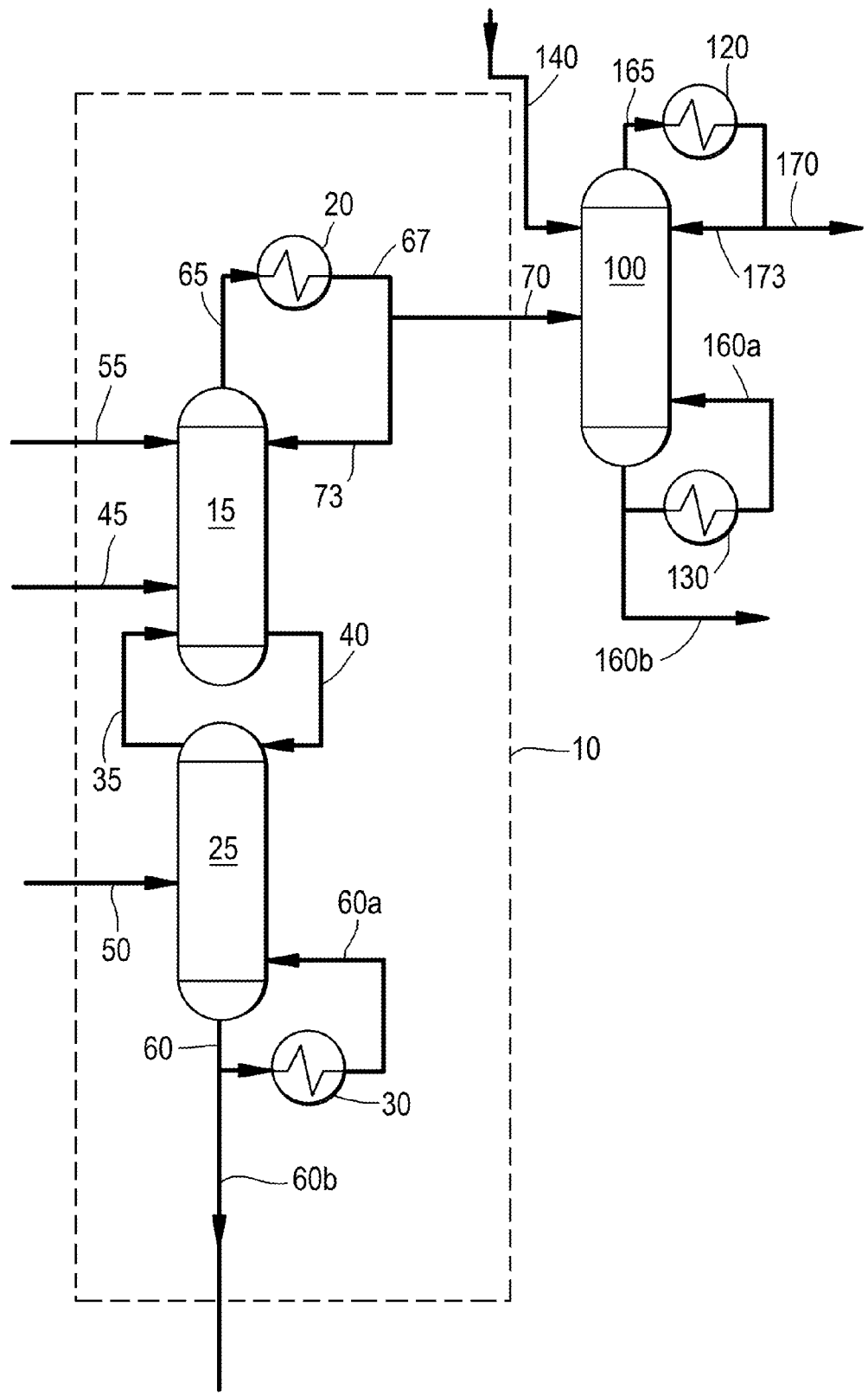

PROCESS FOR REMOVING OXYGENATE FROM AN OLEFIN STREAM

This application claims the benefit of European Application No. 12199677.1 filed Dec. 28, 2012, which is incorporated herein by reference.

FIELD OF THE INVENTION

The present invention relates to a process for removing oxygenate from an olefin stream.

BACKGROUND OF THE INVENTION

Conventionally, ethylene and propylene are produced via steam cracking of paraffinic feedstocks including ethane, propane, naphtha and hydrowax. An alternative route to ethylene and propylene is an oxygenate-to-olefin (OTO) process. Interest in OTO processes for producing ethylene and propylene is growing in view of the increasing availability of natural gas. Methane in the natural gas can be converted into for instance methanol or dimethylether (DME), both of which are suitable feedstocks for an OTO process.

In an OTO process, an oxygenate such as methanol is provided to a reaction zone of a reactor comprising a suitable conversion catalyst whereby the oxygenate is converted to ethylene and propylene. In addition to the desired ethylene and propylene, a substantial part of the oxygenate, such as methanol, is converted to higher hydrocarbons including C4+ olefins and paraffins. The effluent from the reactor comprising the olefins, any unreacted oxygenates such as alcohols or ethers, particularly methanol and dimethylether and other reaction products such as water may then be treated to provide separate component streams. Unreacted oxygenates, in particular methanol, can be separated to a certain extent from the reaction effluent, for instance by contacting with a cooled aqueous stream in a quench zone.

In order to increase the ethylene and propylene yield of the process, the C4+ olefins may be recycled to the reaction zone or alternatively further cracked in a dedicated olefin cracking zone to produce further ethylene and propylene.

In patent application WO 03/020678, a process for the removal of dimethylether from an olefinic stream is disclosed. In the process of WO 03/020678, the olefinic stream comprising dimethylether is first separated into a first stream comprising dimethylether and lighter boiling point compounds and a second stream comprising C4+ olefin and higher boiling point hydrocarbons. The stream comprising dimethylether is subjected to an extractive distillation using an extraction solvent to remove at least part of the dimethylether. Methanol may for instance be used as a solvent.

A similar process is described in US patent application No. 20090223870, a liquid phase containing hydrocarbons and oxygenates is charged to a separation vessel and separated into a light gaseous fraction and a heavier C4+ fraction. The light gaseous fraction together with a gaseous stream is subjected to an extractive distillation with an extraction solvent, which dissolves the oxygenates, to remove at least part of the oxygenates from the combined gaseous stream. The preferred solvents are methanol or NMP.

Where a gaseous stream is contacted with a liquid solvent, inevitably part of the liquid solvent will evaporate, due to its vapour pressure. As a result the combined gaseous stream is contaminated with the solvent. Although NMP has the advantage that it has a low vapour pressure, i.e. as much as 100 times lower than methanol, a disadvantage of using NMP is that it is typically not readily available at the process site and thus must be provided externally.

Methanol may be more readily available to use as solvent, however, due to the high vapour pressure of the methanol, the light olefin rich, dimethylether lean overhead vapour stream will comprise substantial amounts of methanol as a contaminant. When methanol is diluted in a non-polar environment, such as the light olefin rich overhead vapour stream, its properties are no longer determined by its ability to form hydrogen bonds with other polar compounds. Rather, the methanol properties are determined based on its molecular weight. Consequently, methanol when diluted in a non-polar environment behaves similar to a C3 hydrocarbon. In the subsequent treatment of the light olefin rich, dimethylether lean overhead vapour stream to isolate ethylene and propylene product streams such diluted methanol will accumulate in the ethylene and propylene product streams. Methanol-contaminated ethylene and propylene is less suitable as a feedstock for preparing olefin derivatives such as polyethylene or polypropylene. Removing, the diluted methanol from the ethylene and propylene product is difficult and energy consuming.

Nowowiejski et al. (Nowowiejski et al., An overview of oxygenates in olefins units in relation to corrosion, fouling, product specifications, and safety, Presentation at American Institute of Chemical Engineers 2003 Spring National Meeting, New Orleans, USA, in particular page 16) disclose the risk of methanol breakthrough in a C3 splitter even where the feed to the C3 splitter only contains small amounts of methanol. According to Nowowiejski et al., methanol, entering a C3 splitter producing a polymer grade propylene product, will concentrate in the C3 splitter around the 90 to 95 percent propylene zone in the C3 splitter. If methanol levels in the C3 splitter build up over time, a minor upset or change in operating conditions may result in off-spec methanol contaminated propylene product.

U.S. Pat. No. 7,132,580 discloses a methanol to olefin catalytic conversion process including the selective recovery and recycle of dimethylether and methanol from the effluent stream of the reactor. After the reactor effluent stream is charged to a quench zone, the resulting cooled overhead vapour stream can be compressed. The compressed stream can then be passed to a separation zone to recover a vapour stream which is then passed to a dimethylether absorption zone. The vapour stream is contacted with a dimethylether selective solvent containing methanol at scrubbing conditions effective to produce a liquid solvent bottom stream containing methanol, dimethylether, water and substantial and undesired amounts of ethylene and propylene and a light olefin rich, dimethylether lean overhead vapour stream containing methanol.

The liquid solvent bottom stream further treated to remove a substantial portion of ethylene and propylene contained in the stream. According to U.S. Pat. No. 7,132,580, the use of a dimethylether selective solvent containing methanol in the dimethylether absorption zone necessarily results in a vapour stream that is saturated with methanol at the conditions prevailing at the top of the dimethylether absorption zone. As mentioned above, due to the properties of the diluted methanol in the light olefin rich, dimethylether lean overhead vapour stream, part of the methanol will end up as a contaminant in the ethylene and propylene product streams. Consequently, unless additional steps are taken to rigorously remove methanol from the light olefin rich, dimethylether lean overhead vapour stream, the light olefin product may be contaminated with methanol. The process of U.S. Pat. No. 7,132,580 therefore requires a secondary methanol absorption zone in which the light olefin rich, overhead vapour stream is contacted with an aqueous solvent at scrubbing conditions to remove methanol to produce a dimethylether-lean and methanol-lean overhead vapour product stream comprising ethylene and propylene and a bottom stream containing methanol and aqueous solvent. A disadvantage of using an aqueous solvent for removing the methanol from the light olefin rich, overhead vapour stream is that although the methanol may effectively be removed, water may be introduced in the dimethylether-lean and methanol-lean overhead vapour product stream. The introduction of water is undesired as also with water, similar to methanol, when diluted in a non-polar environment, such as a light olefin rich overhead vapour stream, its properties are no longer determined by its ability to form hydrogen bonds with other polar compounds. Rather the water properties are determined based on its molecular weight. Consequently, water when diluted in a non-polar environment accumulates in the low boiling fractions. Generally spoken it is undesirable to have water accumulating in the lower boiling fractions as the water may accumulate as ice in the cold sections of the separation section, while at the same time the introduction of water may lead to corrosion of metal surfaces in the separation section. Therefore, commonly, water is removed from an effluent stream prior to the removal of dimethylether removal. Water present in the low boiling fraction is subsequently removed by drying the low boiling fraction, typically using mol sieve drying beds. The mol sieve beds need to be periodically regenerated, which is an energy consuming process. The frequency of the regeneration required is dependent on the water content in the low boiling fraction.

A need exists to provide an improved process for the removal of dimethylether from hydrocarbon streams, in particular hydrocarbons streams containing ethylene and propylene. Preferably, a process that mitigates the contamination of the light olefin rich overhead vapour stream with water.

SUMMARY OF THE INVENTION

It has now been found that the problems encountered with the prior art processes can be solved by utilising a non-aqueous C2 to C4 alcohol solvent to remove methanol introduced during an earlier methanol wash step to remove dimethylether from an olefin stream. In contrast to the process of U.S. Pat. No. 7,132,580, the use of such non-aqueous C2 to C4 alcohol solvent does not introduce water into the olefin stream.

The process of the present invention is particularly suitable to be combined with an oxygenate to olefin (OTO) process, wherein at least part of the effluent of the OTO process is treated to remove oxygenates. An additional advantage is that the spent solvent comprising C2 to C4 alcohols and absorbed methanol from the olefin stream can be used as feed to the OTO process to yield additional light olefins.

Furthermore, the present invention can provide an integrated process, wherein the non-aqueous C2 to C4 alcohol solvent comprises tertbutanol and the tert-butanol can be prepared from the olefin product of an OTO process. As such the need to provide an additional external solvent is removed as the solvent may be prepared in-situ.

Accordingly, the present invention provides a process for removing dimethylether from an olefin stream comprising dimethylether, comprising:

a) providing to an oxygenate recovery zone the olefin stream comprising dimethylether and a methanol-comprising solvent, treating the olefin stream comprising dimethylether with the methanol comprising solvent, and retrieving at least a dimethylether-depleted, methanol-comprising olefin stream; and b) providing to the oxygenate recovery zone a non-aqueous C2 to C4 alcohol solvent and treating the dimethylether-depleted, methanol-comprising olefin stream with the non-aqueous C2 to C4 alcohol solvent, and retrieving from the oxygenate recovery zone at least an olefinic product that is depleted in dimethylether and methanol and a spent solvent comprising at least one C2 to C4 alcohol and methanol.

BRIEF DESCRIPTION OF THE DRAWINGS

FIG. 1 depicts a diagrammatic scheme of one embodiment of a process for removing oxygenate from an olefin stream comprising oxygenate described herein.

While the invention is susceptible to various modifications and alternative forms, specific embodiments thereof are shown by way of example in the drawings and will herein be described in detail. It should be understood that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The process described herein is a process for removing dimethylether from an olefin stream comprising dimethylether. The process according to the invention is advantageous because methanol introduced in the olefin stream during a first methanol wash is removed using a non-aqueous C2 to C4 alcohol solvent, rather than the aqueous solvent containing described in U.S. Pat. No. 7,132,580. Unlike water, the alcohols described herein have a low volatility, also in dilute mixtures, such that the alcohols described herein are separated from the light hydrocarbons more easily and requiring significantly less energy.

Reference herein to C2 to C4 alcohol is to ethanol, 1-propanol (n-propanol), 2-propanol (iso-propanol), 1-butanol, 2-butanol, 2-methyl-1-propanol (isobutanol), 2-methyl-2-propanol (tert-butanol) or a mixture of two or more thereof.

Reference herein to a non-aqueous C2 to C4 alcohol solvent is to a non-aqueous solvent comprising one or more of ethanol, 1-propanol (n-propanol), 2-propanol (iso-propanol), 1-butanol, 2-butanol, 2-methyl-1-propanol (isobutanol) and 2-methyl-2-propanol (tert-butanol).

Reference herein to a non-aqueous solvent is to a solvent that does not comprise significant amounts of water. Although the solvent preferably, comprises no water, some water may be introduced into the solvent during the preparation of the solvent or due to re-use of a solvent which was recycled. Preferably, a non-aqueous solvent refers to a solvent comprising less than 5 wt % of water, more preferably less than 1 wt %, even more preferably less than 0.1 wt % of water, based on the weight of the non-aqueous C2 to C4 alcohol solvent.

Reference herein to an olefin stream is to a stream comprising at least olefins.

Reference herein to an olefinic stream is to a stream comprising at least olefins.

Reference herein to a spent solvent is to a solvent that has been in contact with an olefin stream. Where the spent solvent refers to spent non-aqueous C2 to C4 alcohol solvent, this spent solvent is a solvent that has been in contact with an olefin stream comprising methanol. This spent solvent comprises at least part of the methanol. The methanol herein is methanol that was provided to the olefin stream during the treatment of the olefin stream comprising dimethylether with a methanol-comprising solvent. The spent solvent will further comprise one or more C2 to C4 alcohols that were provided to the process as part of the non-aqueous C2 to C4 alcohol solvent. Where spent solvent refers to spent methanol-comprising solvent, this spent solvent is a solvent that has been in contact with an olefin stream comprising dimethylether. This spent solvent comprises at least part of the dimethylether.

Reference herein below to the solvent according to the invention is to the non-aqueous C2 to C4 alcohol solvent.

The process according to the present invention is particularly preferred for treating olefin stream comprising dimethylether containing no more than 10 wt %, more preferably 5 wt %, even more preferably 1 wt %, still more preferably 0.5 wt %, even still more preferably 0.1 wt % of dimethylether based on the olefin stream comprising dimethylether.

The olefin stream comprising dimethylether, may be any olefin stream comprising dimethylether. Preferably, the olefin stream comprises at least 25 wt % olefin, more preferably 50 wt % olefin, even more preferably at least 60 wt % olefin, and still more preferably at least 70 wt % olefin, based on the olefins in the olefin stream comprising dimethylether. It is particularly preferred that olefin stream comprising dimethylether comprises at least 25 wt % ethylene and/or propylene, more preferably 50 wt % ethylene and/or propylene, even more preferably at least 60 wt % of ethylene and/or propylene, and still even more preferably at least about 70 wt % of ethylene and/or propylene, based on the olefins in the olefin stream comprising dimethylether. In a preferred embodiment, the olefin stream comprising dimethylether comprises at least 50 wt % propylene, even more preferably at least 60 wt % of propylene, and still even more preferably at least about 70 wt % of propylene, based on the olefins in the olefin stream comprising dimethylether.

A preferred olefin stream comprising oxygenates is an olefin stream comprising oxygenates obtained from an oxygenate to olefins process.

In the process according the invention the dimethylether is removed from the olefin stream comprising dimethylether by providing the olefin stream comprising dimethylether to an oxygenate recovery zone. In addition, a methanol-comprising solvent is provided to the oxygenate recovery zone. The olefin stream comprising dimethylether is treated with the methanol-comprising solvent to remove at least part of the dimethylether from the olefin stream. Methanol is a good absorbent for dimethylether and its use as absorbent (or solvent) for dimethylether present in hydrocarbon streams is well known in the art. The methanol-comprising solvent may be any methanol-comprising solvent, preferably comprising in the range of from 50 to 100 wt % of methanol, based on the weight of the total solvent. More preferably, the methanol-comprising solvent comprises in the range of from 80 to 100 wt % of methanol, based on the total solvent. Optionally, the methanol solvent may comprise one or more of water, ethanol, n-propanol, iso-propanol, 1-butanol, 2-butanol, isobutanol or tert-butanol. The most preferred methanol-comprising solvent consists of methanol, whereby it is noted that the solvent consisting of methanol may comprise minor amounts of other compounds introduced when the methanol-comprising solvent is recycled.

When treating the dimethylether-comprising olefin stream with the methanol-comprising solvent, the dimethylether content in the olefin stream is reduced, however, at the same time methanol is introduced in the olefin stream and a dimethylether-depleted, methanol-comprising olefin stream is retrieved.

The dimethylether-depleted, methanol-comprising olefin stream preferably contains less than 100 ppmv, more preferably less than 75 ppmv, even more preferably less than 50 ppmv of dimethylether, based on the hydrocarbons in the dimethylether-depleted, methanol-comprising olefin stream.

The dimethylether-depleted, methanol-comprising olefin stream may comprise up to 20 wt % of methanol, based on the hydrocarbons in the dimethylether-depleted, methanol-comprising olefin stream. However, preferably, the dimethylether-depleted, methanol-comprising olefin stream comprises less than 10 wt % of methanol, more preferably in the range of from 0.01 wt % to 10 wt % of methanol, based on the hydrocarbon content in the dimethylether-depleted, methanol-comprising olefin stream.

In addition to the methanol-comprising solvent, a further non-aqueous C2 to C4 alcohol solvent is provided to the oxygenate recovery zone. Following the treatment of the olefin stream comprising dimethylether with the methanol-comprising solvent to retrieve the dimethylether-depleted, methanol-comprising olefin stream, this stream is subsequently treated with the non-aqueous C2 to C4 alcohol solvent to remove at least part of the methanol from the dimethylether-depleted, methanol-comprising olefin stream.

Preferably, the non-aqueous C2 to C4 alcohol solvent comprises in the range of from 80 to 100 wt % of C2 to C4 alcohol, based on the total solvent. More preferably, the non-aqueous C2 to C4 alcohol solvent consists of C2 to C4 alcohols. This has the advantage that it reduces the complexity of the solvent and the separation of the solvent from the olefin stream. This advantage becomes more pronounced when the non-aqueous C2 to C4 alcohol solvent comprises no more than two and preferably only one C2 to C4 alcohol.

Preferred C2 to C4 alcohols are ethanol, n-propanol, isobutanol and tert-butanol. N-propanol, isobutanol and tert-butanol being most preferred due to their lower vapour pressure compared to ethanol, which will allow for a more energy efficient separation of the solvent from the olefinic product.

In one preferred embodiment, where the olefin stream comprising dimethylether in addition comprises isobutene, it is preferred that the non-aqueous C2 to C4 alcohol solvent comprises at least tert-butanol, more preferably comprises tert-butanol as the only C2 to C4 alcohol. Tert-butanol can conveniently be produced by reacting isobutanol with water over an acidic catalyst, as described further herein below. In such an embodiment there is no need to provide the non-aqueous C2 to C4 alcohol solvent externally, rather the non-aqueous C2 to C4 alcohol solvent may be produced on-site.

Following the treatment of the dimethylether-depleted, methanol-comprising olefin stream with the non-aqueous C2 to C4 alcohol solvent an olefinic product that is depleted in dimethylether and methanol is retrieved from the oxygenate recovery zone. In addition, separately, a spent solvent comprising at least one C2 to C4 alcohol and methanol is retrieved from the oxygenate recovery zone.

The C2 to C4 alcohols are suitable solvents for methanol, while having low vapour pressures compared to e.g. water and methanol, in particular in diluted form in non-polar hydrocarbon environments. Consequently, these solvents do not or at least to a much lesser extent affect the purity of a resulting propylene product, as they can be separated easily from the propylene in a distillation process. An additional advantage of the solvent according to the invention compared to the use of water based solvents is that at least part the residual dimethylether still present in the dimethylether-depleted, methanol-comprising olefin stream may be removed together with the methanol. The C2 to C4 alcohols are good solvents for dimethylether. A further advantage of the solvent according to the invention is that the C2 to C4 alcohols are also good solvents for water. As such the C2 to C4 alcohols may also remove any residual water present in the dimethylether-depleted, methanol-comprising olefin stream. This has the advantage that the need for additional mol sieve based drying of the olefinic product is reduced if not removed, thereby reducing the required frequency and energy consumption of the mol sieve bed regeneration.

Preferably, the dimethylether-depleted, methanol-comprising olefin stream is treated with the non-aqueous C2 to C4 alcohol solvent at a pressure of from 2.5 to 350 bara. More preferred operating pressure ranges are of from 5 to 60 bara, even more preferably 10 to 50 bara. Preferably, the dimethylether-depleted, methanol-comprising olefin stream is treated with the solvent according to the invention at a temperature in the range of from 0 to 60° C., preferably of from 25 to 60° C. Where the solvent according to the invention comprises tert-butanol, it is preferred that the olefins stream comprising oxygenate is treated with the solvent at a temperature in the range of from 25 to 60° C. Preferably, the dimethylether-depleted, methanol-comprising olefin stream is treated with the non-aqueous C2 to C4 alcohol solvent below the boiling point of the non-aqueous C2 to C4 alcohol solvent and its individual components, and above the boiling point of at least part of the components in dimethylether-depleted, methanol-comprising olefin stream at the operating conditions prevailing in the oxygenate recover zone.

The dimethylether-depleted, methanol-comprising olefin stream is contacted with the non-aqueous C2 to C4 alcohol solvent in the oxygenate recovery zone to obtain an oxygenate-depleted product stream comprising olefin and a spent solvent.

In the process according to the invention, the olefin stream comprising dimethylether is preferably treated with the methanol-comprising solvent under the conditions as described herein above for the treatment of the dimethylether-depleted, methanol-comprising olefin stream with the non-aqueous C2 to C4 alcohol solvent. However, within the oxygenate recovery zone the treatment of the olefin stream comprising dimethylether and the dimethylether-depleted, methanol-comprising olefin stream may be different.

The oxygenate recovery zone may comprise two or more extraction and/or separation steps. Preferably, the olefin stream comprising dimethylether is contacted with the methanol-comprising solvent to extract at least part of the dimethylether in the olefin stream. Subsequently, the dimethylether-depleted, methanol-comprising olefin stream is treated with the non-aqueous C2 to C4 alcohol solvent to remove any methanol that was carried over.

The olefin stream comprising oxygenate may be contacted with the solvent according to the invention in any suitable way, including but not limited to liquid-gas contactors, bubble columns, wash columns and extractive distillation columns. In one preferred embodiment, the treatment of olefin stream comprising dimethylether with the methanol-comprising solvent is done using a extractive distillation process, while the treatment of the dimethylether-depleted, methanol-comprising olefin stream is done using a solvent wash. The difference between the extractive distillation and the solvent wash lies manly in the recycle of the solvent in the process. For the removal of methanol from the dimethylether-depleted, methanol-comprising olefin stream, a solvent wash may be sufficient. In another preferred embodiment, both the treatment of the olefin stream comprising dimethylether with the methanol-comprising solvent and the treatment of the dimethylether-depleted, methanol-comprising olefin stream with the non-aqueous C2 to C4 alcohol solvent are done separately in two or more extractive distillation processes. The extractive distillation processes may take place in an extractive distillation vessel or column, which can be of conventional design. Preferably, a packed distillation column is used. Using an extractive distillation for the treatment of both the olefin stream comprising dimethylether and the dimethylether-depleted, methanol-comprising olefin stream, the removal of dimethylether and, respectively, methanol may further improved.

Preferably, the extractive distillation process is carried out at a pressure of from 2.5 to 350 bara. More preferred operating ranges are of from 5 to 60 bara; even more preferably 10 to 50 bara. By setting the operating pressure of the extractive distillation vessel at higher pressures, more dimethylether, respectively methanol, is removed from each of the olefin streams.

An extractive distillation process is preferred, for instance over a wash column, as the combination of energy input and solvent addition improves the separation between the components, allowing for an effective removal of even very low concentrations of dimethylether, respectively methanol, present in an olefin stream and reducing the losses of valuable components in the solvent. It may preferably be used for removing of dimethylether, respectively methanol from olefin streams comprising no more than 20 wt % of dimethylether, respectively methanol, based on weight of the respective olefin streams. The use of an extractive distillation process to treat the respective olefin streams with the methanol-comprising solvent and respectively the non-aqueous C2 to C4 alcohol solvent is particularly preferred for treating olefin streams containing no more than 10 wt %, more preferably 5 wt %, even more preferably 1 wt %, still more preferably 0.5 wt %, even still more preferably 0.1 wt % of dimethylether, respectively methanol, based on the respective olefin streams.

The extractive distillation process is preferably operated below the boiling point of the solvent and its individual components, and above the boiling point of at least part of the components in olefinic stream comprising oxygenate at the operating conditions prevailing in the distillation column. It is preferred to operate the process such that the formation of two liquid phases in the column is prevented. As the solvent travels through the distillation column dimethylether, respectively methanol, are absorbed into the solvent and removed along with the solvent at the bottom of the extractive distillation column. The extractive distillation process herein may comprise one or more stages and one or more columns, optionally with intermediate reheating or cooling.

Typically, extractive distillation will be operated to allow the C3− olefins in the olefin stream to be retrieved as a top effluent from the extractive distillation, while the spent solvent, being either spent methanol-comprising solvent or the spent solvent comprising al least C2 to C4 alcohol and methanol, is retrieved as a bottom stream.

The oxygenate recovery zone may be operated separately or may be combined with one or more other distillation processes. The oxygenate recovery zone may be operated in series with one or more de-ethaniser, de-propaniser, de-butaniser or de-pentaniser columns, which respectively separate an olefin stream in a C2− and C3+ fraction, C3− and C4+ fraction, C4− and C5+ fraction, and C5− and C6+ fraction. In one embodiment, the olefin stream comprises propylene and propane next to the dimethylether and the treatment of the olefins stream comprising dimethylether is combined with a propylene/propane separation column, also known as a PP splitter. In another embodiment, where the olefin stream comprises at least C3 and C4 olefins next to the dimethylether, the treatment of the olefins stream comprising dimethylether is combined with a C3−/C4+ separation column, also known as a de-propaniser column.

The spent solvent comprising C2 to C4 alcohols and methanol may be regenerated by removing at least part to the methanol or be used for other purposes.

In a particular embodiment, the olefin stream comprising dimethylether is prepared as part of a reaction effluent stream of an oxygenate to olefins reaction zone wherein an oxygenate feedstock is converted as part of an oxygenate to olefins process. Such a reaction effluent of an oxygenate to olefins reaction zone of an oxygenate to olefins process typically comprises olefins and an amount of dimethylether. This dimethylether may be unreacted dimethylether that was provided to the oxygenate to olefins reaction zone as part of an oxygenate feedstock, however, they may also be a reaction product formed inside the oxygenate to olefins reaction zone.

In a further embodiment, where the olefin stream comprising dimethylether is prepared as part of a reaction effluent stream of an oxygenate to olefins reaction zone wherein an oxygenate feedstock is converted as part of an oxygenate to olefins process, and wherein prior to step (a) the process comprises at least the steps of:

v) reacting an oxygenate feedstock in an oxygenate reaction zone in the presence of a catalyst comprising a molecular sieve to produce a reaction effluent stream comprising dimethylether, olefin and water; and vv) separating the reaction effluent stream into a water rich stream comprising water and an olefin stream comprising dimethylether.

Reference herein to an oxygenate feedstock is to a feedstock comprising oxygenates. The oxygenates in the feedstock may include dimethylether.

It is a particular advantage of the present process that the non-aqueous C2 to C4 alcohol solvent itself can be used as a feedstock to an OTO process. Therefore, in a further embodiment, the process further comprises the step of:

(c) passing at least a portion of the spent solvent comprising at least one C2 to C4 alcohol and methanol to the oxygenate to olefins reaction zone together with or as part of the oxygenate feedstock.

In addition at least part of the spent methanol comprising solvent may also be provided to the oxygenate reaction zone together with or a part of the oxygenate feedstock.

The reaction effluent stream obtained from the OTO reaction zone, typically comprises substantial amounts of ethylene and propylene. OTO processes according to the present invention preferably produce a reaction zone effluent comprising at least 25 wt % of ethylene and propylene based on the olefin content in the reaction effluent. In addition to ethylene and propylene, the reaction effluent from the OTO also, preferably comprises C4 iso-olefins, i.e. isobutene. The isobutene may be used to prepare tert-butanol by a reaction with water. Water is readily available as a by-product of the OTO process. A particular advantage of the use of a tert-butanol based solvent is that it can be produced solely from reaction by-products.

Therefore, in a preferred embodiment, the reaction effluent stream obtained from the OTO reaction zone further comprises C4 tertiary iso-olefins and at least part of the C4 tertiary iso-olefins is reacted with water to tert-butanol to provide a tert-butanol-comprising stream. Preferably, the water is at least in part obtained as part of the effluent from the OTO process.

When the spent solvent is recycled to the OTO reaction zone together with or as part of the oxygenate feedstock, the C4 tertiary iso-olefins which were converted to solvent components may further be converted to additional ethylene and propylene, thereby further increasing the ethylene and propylene yield of the OTO process.

In another embodiment, the reaction of the C4 tertiary iso-olefins with water can be carried out in the presence of an acidic catalyst, such as an acidic ion exchange resin, preferably Amberlyst 15. The reaction conditions of these to processes are well known in the art and do not need any further explication herein. Reference is made to for instance US7002050B2, for processes and process conditions for the catalytic hydration of C4 tertiary iso-olefins to tert-butanol.

As mentioned above, it is a particular advantage of the process according to the present invention that the solvent may be prepared from products provided by an OTO process. The thus produced tert-butanol may be passed to the oxygenate recovery zone together with or as part of the non-aqeous C2 to C4 alcohol solvent. Preferably, the tert-butanol is treated to remove any water prior to being passed to the oxygenate recovery zone.

An advantage of using the solvent according to the present invention is that the C2 to C4 alcohols and have a lower vapour pressure than methanol in particular diluted form, more particular when present in diluted from in a non-polar hydrocarbon environment. As a result, the C2 to C4 alcohols are not transported to the olefinic vapour phase to the extent water is, i.e. under equal conditions. By not using water the need to provide additional drying to remove water from the olefinic product is reduced if not removed. Any solvent according to the present invention that is transported to the olefinic vapour phase may removed from the olefinic vapour phase at significantly less energy cost than water and without having to accept the corrosion issues of experienced with water. Rather, these C2 to C4 alcohols are preferably directed to the C4+ fractions.

Where tert-butanol is used as, part of, the solvent, it must be realised that tert-butanol is a solid below 25° C. and 1 bara, therefore in order to use tert-butanol as part of the solvent the temperature at which the olefin stream comprising oxygenate is treated must be higher than 25° C., in case the solvent is pure tert-butanol.

As mentioned herein above, the process according to the invention is particularly useful to be combined with an oxygenate-to-olefin process or OTO process. In an OTO process oxygenates, preferably oxygenates such as methanol and dimethylether are converted over a molecular sieve catalyst to at least ethylene and propylene. The ethylene and propylene are retrieved from the OTO process as part of an olefin stream, which typically also comprises C4+ olefins, paraffins and dimethylether. The dimethylether may be unreacted feed dimethylether or may have been formed during the OTO process.

OTO process are well known in the art and have for instance been described in WO A 2006/020083. Processes integrating the production of oxygenates from synthesis gas and their conversion to light olefins are described in US20070203380A1 and US20070155999A1.

The oxygenate used in an oxygenate feedstock provided to the OTO process is preferably an oxygenate which comprises at least one oxygen-bonded alkyl group. The alkyl group preferably is a C1-C5 alkyl group. Preferably, the oxygenate is methanol or dimethylether, or a mixture thereof. The oxygenate feedstock may also comprise ethanol in addition to methanol or dimethylether, preferably in an amount of less than 50 wt %. Where oxygenate feedstock comprises ethanol, it is preferred that the solvent according to the invention also comprises ethanol. More preferably, in that case the ethanol in the oxygenate feedstock is provided by passing at least part of a solvent according to the invention comprising ethanol is passes to the OTO process as part of the oxygenate feedstock. Particularly preferred ethanol is bio-ethanol.

A diluent, such as water or steam, may also be provided to the OTO process together with or as part of the oxygenate feedstock. Preferably, in addition to the oxygenate and diluent, an olefinic co-feed is provided along with and/or as part of the oxygenate feedstock. The olefinic co-feed preferably comprises C4+ olefins i.e. C4 and higher olefins, more preferably C4 and C5 olefins. Preferably, at least part of the olefinic co-feed, during normal operation, is formed by a recycle stream of a C4+ hydrocarbon fraction from the OTO reaction effluent, i.e. the olefin stream obtained from the OTO process. In order to maximize production of ethylene and propylene, it is desirable to maximize the recycle of C4 olefins in the effluent of the OTO process as these olefins are converted to further ethylene and propylene. Where reference is made to an OTO process, this is to process that produces significant amounts of ethylene and propylene by converting at least part of the feedstock. Preferably, olefin steam, as obtained from the OTO process, comprises at least 50 wt % of ethylene and/or propylene, based on the hydrocarbon content of the olefin steam.

Catalysts suitable for converting the oxygenate feedstock comprise one or more molecular sieves. Such molecular sieve-comprising catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing tetrahedral units, more preferably, two or more [SiO4], [AlO4] and/or [PO4] tetrahedral units. These silicon, aluminum and/or phosphorus based molecular sieves and metal containing silicon, aluminum and/or phosphorus based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å. Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanides of the Periodic Table of Elements. Preferably Me is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, and the FER type. Other suitable zeolites are for example zeolites of the STF-type, such as SSZ-35, the SFF type, such as SSZ-44 and the EU-2 type, such as ZSM-48.

Aluminosilicate-comprising catalyst, and in particular zeolite-comprising catalyst are preferred when an olefinic co-feed is fed to the oxygenate conversion zone together with oxygenate, for increased production of ethylene and propylene.

Preferred catalysts for OTO processes comprise SAPO, MEL and/or MFI type molecular sieves, whereby the latter two are zeolite molecular sieves. More preferred catalyst comprise SAPO-34, ZSM-11 and/or ZSM-5 type molecular sieves. A preferred MFI-type zeolite for the OTO catalyst has a silica-to-alumina ratio, SAR, of at least 60, preferably at least 80. More preferred MFI-type zeolite has a silica-to-alumina ratio, SAR, in the range of 60 to 150, preferably in the range of 80 to 100.

The catalyst may further comprise phosphorus as such or in a compound, i.e. phosphorus other than any phosphorus included in the framework of the molecular sieve. It is preferred that a MEL or MFI-type zeolite comprising catalyst additionally comprises phosphorus.

The reaction conditions of the oxygenate conversion, include a reaction temperature of 350 to 1000° C., preferably from 350 to 750° C., more preferably 450 to 700° C., even more preferably 500 to 650° C.; and a pressure from 0.1 kPa (1 mbara) to 5 MPai (50 bara), preferably from 100 kPa (1 bara) to 1.5 MPa (15 bara).

Preferably, the oxygenate feedstock is preheated to a temperature in the range of from 200 to 550° C., more preferably 250 to 500° C. prior to contacting with the molecular sieve-comprising catalyst.

The olefin stream exiting the OTO process may be suitably treated to remove dimethylether from such stream by the process according to the present invention. Preferably, prior to passing the olefin stream comprising dimethylether to the oxygenate recovery zone the olefin stream comprising dimethylether is treated to remove water and heavy (C7+) hydrocarbons. The olefin stream may, prior to passing the olefin stream comprising dimethylether to the oxygenate recovery zone, further be treated to remove low boiling fractions such as methane, hydrogen and carbon oxides.

The olefin stream comprising dimethylether, preferably after water has been removed, can be passed to a compressor, in which the pressure of the stream is increased. In one embodiment of the invention, the treatment of the olefin stream comprising dimethylether with the methanol-comprising solvent occurs immediately after quenching and preferably compressing of the olefin steam comprising dimethylether obtained from the OTO process. In another embodiment, the olefin stream comprising dimethylether is optionally treated, typically in two or more separate columns, to remove a C2-hydrocarbon fraction and optionally a C4+ fraction. Preferably, at least an olefin stream comprising C3 hydrocarbon fraction is treated with the methanol-comprising solvent, as most of the dimethylether will be part of the C3 hydrocarbon fraction.

The spent solvent comprising at least a C2 to C4 alcohol and methanol can, at least in part, be passed to the OTO process. This could, for instance, be done as a part of an olefinic co-feed stream.

Where herein it is mentioned that the olefin stream comprising dimethylether is obtained from the effluent of an oxygenate to olefins process, such a olefin stream may also be obtained from the combined effluent of a oxygenate to olefin process and a steam cracking process.

DETAILED DESCRIPTION OF THE FIGURE

In FIG. 1, there is shown de-propaniser 10 consisting of high-pressure column section 15 with condenser 20 and low-pressure column section 25 with reboiler 30. The top stream of low-pressure column section 25 is provided, while being condensed and pressurised (not shown), to high-pressure column section 15 via means 35, while the liquid bottom steam of high-pressure column section 15 flows to low-pressure column section 25 via means 40. A first olefin stream 45 is provided to high-pressure column section 15. This first feed stream may for instance be obtained from a de-ethaniser column used to separate the C2− fraction from an olefin stream comprising oxygenate for example an olefin stream obtained from a OTO process. A second olefin stream 50 is provided to low-pressure column section 25. This second feed stream may for instance be obtained from the compression section where an olefin stream comprising oxygenate, for example obtained from a OTO process, is compressed in one or more stages of a compressor train or the compression section. In the final stages of the compression of the olefin stream, a liquid hydrocarbon stream condenses out from the olefin stream. This condensate is subsequently stripped in a condensate stripper to remove any entrained C3 and lighter hydrocarbons. These C3 and lighter hydrocarbons are provided to de-propaniser 10. At least one of streams 45 and 55 will comprise dimethylether.

Methanol-comprising solvent stream 55 is provided close to the top of high-pressure section 15 of depropaniser 10.

Of liquid fraction 60 exiting the bottom of low-pressure column section 25, part 60a is passed to reboiler 30 and returned to low-pressure column section 25. Another part 60b is removed and further treated (not shown) to for instance recover the C4+ hydrocarbons and the liquid solvent. Vapor fraction 65 exiting the top of high-pressure column section 15, is passed to condenser 20. Condensed stream 67 is split, with condensed stream 70 being passed to methanol removal column 100, while condensed stream 73 is recycled to high-pressure column section 15.

Where methanol removal column 100 is an extractive distillation column, it may be equipped with condenser 120 and reboiler 130.

A non-aqueous C2 to C4 alcohol solvent 140, such as for instance a tert-butanol solvent, is provided to methanol removal column. Of liquid fraction 160 exiting the bottom of solvent removal column 100, part 160a is passed to reboiler 130 and returned to methanol removal column 100. Another part 160b is removed and further treated (not shown) to for instance recover the non-aqueous C2 to C4 alcohol solvent. Vapor fraction 165 exiting the top of solvent removal column 100, is passed to condenser 120. Condensed stream 170 is retrieved as olefinic product depleted in methanol and dimethylether, while part of condensed stream 170 is recycled as stream 173 to solvent removal column 100.

We claim:

1. A process for removing dimethylether from an olefin stream comprising dimethylether, comprising:
   a) providing to an oxygenate recovery zone the olefin stream comprising dimethylether and a methanol-comprising solvent, treating the olefin stream comprising dimethylether with the methanol comprising solvent, and retrieving at least a dimethylether-depleted, methanol-comprising olefin stream; and
   b) providing to the oxygenate recovery zone a non-aqueous C2 to C4 alcohol solvent and treating the dimethylether-depleted, methanol-comprising olefin stream with the non-aqueous C2 to C4 alcohol solvent, and retrieving from the oxygenate recovery zone at least an olefinic product that is depleted in dimethylether and methanol and a spent solvent comprising at least one C2 to C4 alcohol and methanol.

2. The process of claim 1, wherein the non-aqueous C2 to C4 alcohol solvent comprises at least one of ethanol, n-propanol and tert-butanol.

3. The process of claim 1, wherein the solvent comprises tert-butanol.

4. The process of claim 1, wherein the dimethylether-depleted, methanol-comprising olefin stream is treated with the non-aqueous C2 to C4 alcohol solvent in an extractive distillation process.

5. The process of claim 1, wherein the olefin stream comprising dimethylether is prepared as part of a reaction effluent stream of an oxygenate to olefins process.

6. The process of claim 1, wherein prior to step (a), the process comprises at least the steps of:
   v) reacting an oxygenate feedstock in an oxygenate reaction zone in the presence of a catalyst comprising a molecular sieve to produce a reaction effluent stream comprising dimethylether, olefin and water; and
   vv) separating the reaction effluent stream into a water rich stream comprising water and an olefin stream comprising dimethylether.

7. The process of claim 5, further comprising the step of:
   (c) passing at least a portion of the spent solvent to the oxygenate to olefins reaction zone together with or as part of the oxygenate feedstock.

8. The process of claim 5, wherein:
   i) the non-aqueous C2 to C4 alcohol solvent comprises tert-butanol;
   ii) the reaction effluent stream further comprises C4 tertiary iso-olefin; and
   wherein at least part of the C4 tertiary iso-olefins in the reaction effluent stream is reacted with water to tert-butanol to provide a tert-butanol-comprising stream.

9. The process of claim 8, wherein the process further comprises the step of:
   passing at least a portion of tert-butanol stream to the oxygenate recovery zone together with or as part of the non-aqueous C2 to C4 alcohol solvent.

10. The process of claim 1, wherein the olefin stream comprising dimethylether is compressed prior to being provided to the oxygenate recovery zone.

* * * * *